United States Patent [19]

Vidic

[11] 4,283,530

[45] Aug. 11, 1981

[54] PROCESS FOR THE PREPARATION OF HEPARIN

[75] Inventor: Hans-Jorg Vidic, Berlin, Fed. Rep. of Germany

[73] Assignee: Schering Aktiengesellschaft, Berlin, Fed. Rep. of Germany

[21] Appl. No.: 54,071

[22] Filed: Jul. 2, 1979

Related U.S. Application Data

[63] Continuation of Ser. No. 851,562, Nov. 14, 1977, abandoned.

[30] Foreign Application Priority Data

Nov. 12, 1976 [DE] Fed. Rep. of Germany ....... 2652272

[51] Int. Cl.$^3$ .............................................. C08B 37/10
[52] U.S. Cl. ....................................... 536/21; 424/180
[58] Field of Search ........................... 536/21; 424/180

[56] References Cited

U.S. PATENT DOCUMENTS

| | | | |
|---|---|---|---|
| 2,623,001 | 12/1952 | Sylven | 536/21 |
| 3,058,884 | 10/1962 | Mozen et al. | 536/21 |
| 4,119,774 | 10/1978 | Andersson et al. | 536/21 |

FOREIGN PATENT DOCUMENTS 872214 7/1958 United Kingdom ...................... 536/21

OTHER PUBLICATIONS

Physicians' Desk Reference, Publisher Charles E. Baker, Jr., Medical Economics Co., New Jersey, p. 545, 1980.
Lindahl, U., Biochem. Biophys. Acta., vol. 130, pp. 368-382 (1966).
Kiss, J., Survey article, "Chemical Structure of Heparin", circa, about 1976.
Ehrlich et al., J. Pharm. Sci., vol. 62, p. 517, 1973.

*Primary Examiner*—Johnnie R. Brown
*Assistant Examiner*—Blondel Hazel
*Attorney, Agent, or Firm*—Millen & White

[57] ABSTRACT

Heparin is extracted from intestinal brine, i.e., from the brine which results from the preservation and dewatering treatment of animal tissue with sodium chloride, using conventional methods. The extracted product has a high activity and can subsequently be further purified to yield very high heparin activities.

11 Claims, No Drawings

PROCESS FOR THE PREPARATION OF HEPARIN

This is a continuation, of application Ser. No. 851,562, filed Nov. 14, 1977 now abandoned.

BACKGROUND OF THE INVENTION

The present invention relates to a process for obtaining heparin from natural sources.

Heparin has been available to the medical industry for a long time as a naturally occurring anticoagulant. It is still indispensable in modern medicine and finds an ever broadening range of applications.

In recent years, a number of methods have been developed for isolating heparin from heparin-containing animal tissues, such as lungs, liver, etc., using increasingly mild procedures. Recently, heparin extractions have been made primarily from intestinal slime (mucosa) from pigs, cattle, and sheep (e.g., British Pat. No. 754,885; German Pat. No. 1,228,241; U.S. Pat. No. 3,058,884; and German Pat. No. 1,253,868). Such raw materials have the disadvantage of a limited shelf life since they decompose readily. Although the shelf life can be prolonged by freezing, this is an unsatisfactory solution due to the concomitant considerable increase in expense and the additional technical processing required. Moreover, during the extraction process, the factory personnel as well as the residents in the vicinity are all too often confronted with an intolerable environment due to the unpleasant odor connected with the process. Consequently, there continues to be a need for an alternate method of extracting heparin from natural sources.

SUMMARY OF THE INVENTION

Accordingly, it is an object of this invention to provide a method of extracting heparin from natural sources which is free from the above-mentioned disadvantages of prior art processes.

It is another object of this invention to provide a method of extracting heparin, having high purity and activity, from animal tissue.

Upon further study of the specification and appended claims, further objects and advantages of this invention will become apparent to those skilled in the art.

It has now been found that the brine (intestinal brine) produced in the slaughterhouses and intestinal mucosa processing plants contains heparin. This brine is formed during the step of salting animal intestines, previously freed of intestinal mucosa, with solid table salt for purposes of preservation and dewatering.

As a result, in a method aspect, this invention provides an improved method of extracting heparin from heparin-containing tissue, the method comprising extracting heparin from a heparin-containing source derived from animal tissue, and the improvement comprising using as the heparin-containing source, the brine which is formed by the treatment of the tissue with sodium chloride for purposes of preservation and dewatering.

In another method aspect, this invention involves a method for extracting heparin from animal tissue which comprises treating animal tissue containing heparin with sodium chloride, thereby forming a heparin-containing brine; and extracting the heparin from the brine so formed.

DETAILED DISCUSSION

German Pat. No. 1,253,868 summarizes the preparation of heparin by several conventional processes. According to this description, during the initial stages of these processes, the animal tissue, is brought into contact with a hot, aqueous brine in order to dissolve the heparin out of the tissue cells. The proportion of heparin in the thus-obtained brine medium is extremely low. In view of this German patent, it is therefore extremely surprising that the brine produced during the mere salting of animal intestines for non-heparin extracting purposes contains rather large amounts of heparin. It certainly could not be expected that this heparin is present in a form almost entirely devoid of chemically related by-products, so that this brine, heretofore only known as an ecologically burdensome waste product, represents a new raw material source for heparin in extremely pure forms. This is most significant since heparin is already becoming very rare due to the lack of raw materials.

The prior art methods of salting the animal tissue for purposes of preservation and dewatering are, of course, well known as usual slaughterhouse practice.

Typically, from 0.01 to 0.5 g of sodium chloride per gram of animal tissue are used in the treatment. The contact of the sodium chloride with the animal tissue is generally maintained for from 2 hours to 2 days. The preservation treatment may be accomplished either by direct salting of solid sodium chloride followed by optional storage in water, or by immersion of the tissue in an aqueous sodium chloride brine. In either method, the concentration of NaCl in the intestinal brine is 1 to 5.4 M, preferably 3 to 5.4 M and storage temperatures are 0° to 30° C. In contrast, the conventional hot heparin-extracting brine is employed at a temperature of 50° to 100° C. and has an NaCl concentration of 1 to 3 M.

A skilled slaughterhouse worker frees the intestines from intestinal mucosa. Then the intestines are washed and are placed in a horde. Usually the intestines are salted in such a manner, that there are one layer of intestines to one layer of sodium chloride. During 2 hours to 2 days, the intestinal brine is formed, which was without practical importance, because the salting of intestines had only the purpose of preservation and dewatering but not heparin extracting. The formed intestinal brine is collected in a vessel.

It is preferred that the animal tissue be separated from the preserving brine prior to the extraction of the heparin from this brine. The separated animal tissue can be washed and the washing liquid (water) added to the separated brine prior to extraction of the heparin. The extraction of the heparin from the preservation brine and subsequent further purification are fully conventional and are disclosed, for example, in British Pat. No. 754,885; German Pat. No. 1,228,241; U.S. Pat. No. 3,058,884; German Pat. No. 1,253,868; and German Pat. No. 1,156,938, whose disclosures are incorporated by reference herein.

Advantageously, since the content of impurities in the preservation brine is very low, the brine can be worked up for extraction of crude heparin using particularly mild treatment, thus avoiding the expensive isolation methods of the prior art. (See, for example, U.S. Pat. No. 3,451,996 and British Pat. No. 1,221,784). Moreover, the final quality of the extracted heparin is of a level by far superior to that of the heparin preparations commercially available. The crude heparins isolated from the intestinal brine used as the raw material in this invention employing conventional workup techniques, are obtained with such purity that the subsequent conventional purification step produces heparins with activities far above 200 U.S.P. units per milligram. The heparin preparations now commercially available normally possess values of 150 U.S.P. units per milligram, and in a few rare cases, 155 U.S.P. units per milligram. In this connection, a U.S.P. unit/mg is the specific activity determined by the standard U.S.P. assay by measuring the inhibition of clot formation in preserved sheep plasma. 1 U.S.P. unit corresponds approximately to 1.1 international units (IU). Since, despite numerous improvements in the preparative method, the activity values of the commercially available heparin preparations are still unsatisfactory, the U.S.P. prescribes, for example, that heparin preparations (from intestinal mucosa) must contain at least 140 U.S.P. units. Heretofore, even in the laboratory, it has only been possible to isolate heparin with a maximum activity of 175 U.S.P. units/mg, using repeated crystallizations as a barium salt. (L. W. Kananagh and L. B. Jaques, *Arzneimittelforschung (Drug Res.)*, 24, No. 12, 1942 (1974)).

By using intestinal brine as a raw material in accordance with the present invention, it has been made possible to isolate heparin on an industrial scale with a purity wherein it is present as an almost colorless substance, e.g., of an activity greater than 180, and even greater than 250 U.S.P. units/mg. In contrast, all crude heparins available today from other raw materials must first be decolorized by expensive and wasteful processes (U.S. Pat. No. 3,179,566). Moreover, brine is an almost odorless raw material which can be stored and does not suffer from any deterioration in quality over long storage times. Consequently, the need for chemical and other preservation methods are eliminated.

This invention, therefore, relates to the use of intestinal brine as a raw material source for heparin, as well as to a process for the isolation of a particularly pure heparin from brines of animal tissue in accordance with conventional methods, characterized in that intestinal brine is utilized as the starting material.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In each case, the product referred to is, of course, heparin.

EXAMPLE 1

600 liters of brine was combined under agitation with 600 liters of methanol within one-half hour in a 1,500 liter agitator-equipped unit at room temperature. The mixture was agitated for the same time period, whereupon it was allowed to stand for about one hour.

The turbid supernatant liquor was then decanted into a second vessel and the thus-precipitated salt cake was left in the vessel. The thus-obtained suspension was allowed to stand for two days. Thereafter, the suspension was once again decanted, the supernatant liquor was discarded, and the precipitate was isolated by centrifuging. After drying under vacuum, 1.68 kg. of a product was obtained having 11 U.S.P. units/mg. This product still consists of about 60% of sodium chloride.

EXAMPLE 2

In a procedure similar to that described in British Pat. No. 754,885, 3 liters of brine was acidified under agitation with acetic acid to pH 3.1–3.2 (about 50 ml.). After a few hours, the mixture was decanted and the remainder was centrifuged. The precipitate was discarded, and the combined solutions were neutralized with sodium hydroxide solution.

Under agitation, the solution was then gradually combined with the same volume of methanol. After 45 minutes, the mixture was decanted off from the precipitated sodium chloride. This suspension was allowed to stand for several hours, the supernatant liquor was decanted, and the residue was centrifuged. The precipitate was dried under vacuum, thus obtaining 3.76 g. with 23 U.S.P. units/mg.

EXAMPLE 3

3 liters of brine was diluted with 14 liters of water. This solution was combined with 50 g. of kieselguhr, as well as with a solution of 7 g. of benzethonium chloride (=Hyamine 1622, Rohm & Haas) in 100 ml. of water. After a few hours, the mixture was decanted and the residue vacuum-filtered. After washing with water, the still moist precipitate was extracted three times with respectively 200 ml. of 2-molar NaCl solution in accordance with the process disclosed in German Pat. No. 1,228,241. The combined extracts were precipitated with 2 parts by volume of methanol. The isolated and dried precipitate weighed in at 560 mg. and had an activity of 163 U.S.P. units/mg.

EXAMPLE 4

3 liters of brine was brought to pH 3.1–3.2 with acetic acid under agitation. After allowing the mixture to stand for several hours, it was decanted and the residue centrifuged. The combined solutions were diluted with water to 15.5 liters and combined with 40 g. of kieselguhr as well as 7 g. of benzethonium chloride (Hyamine 1622) in 100 ml. of water.

After a few hours, the precipitate was isolated as described in Example 3 and further processed.

Finally, 796 mg. of product was obtained with 105 U.S.P. units/mg.

EXAMPLE 5

3 liters of brine was diluted with 13 liters of water (see German Pat. No. 1,156,938). The solution was then acidified to pH 3.2 with acetic acid (about 50 ml.). After a few hours, a precipitate had separated which, after decanting the clear supernatant liquor, was removed by centrifuging. After drying, 16.6 g. of crude heparin is obtained with 5.5 U.S.P. units/mg.

EXAMPLE 6

10 liters of brine was diluted with 50 liters of water. This solution was pumped through a filter via an ion exchange column having a diameter of 26 mm. and a length of 380 mm. (about 3 l./h.). A medium-basic, macroporous anion exchange resin in the Cl⁻ form was employed (Lewatit CA 9249). It is also possible to use other anion exchange resins, such as, for example, Dowex 1-X-1, described in German Pat. No. 1,253,868.

The resin was then removed from the column, washed twice with 500 ml. of 0.9-molar NaCl solution, and eluted at 40° C. under agitation with 400 ml. of 2-molar NaCl solution for 5 hours. This solution was precipitated with 1.5 parts by volume of methanol. The isolated and dried precipitate weighed 1.5 g. and had 152 U.S.P. units/mg.

EXAMPLE 7

An aliquot of the crude heparin from Example 1 corresponding to 425,000 U.S.P. units and/or 38.65 g., was extracted three times with respectively 200 ml. of 2-molar NaCl solution, each time under one hour of agitation at 60° C. The combined extracts were diluted with water until the solution contained about 0.9 mol/l. of chloride ions. At this point, 200 ml. of an anion exchanger (Lewatit CA 9249) in the chloride form was added to the reaction mixture and the latter stirred for one hour. Thereafter, the mixture was vacuum-filtered and washed with about 200 ml. of 0.9-molar NaCl solution. The ion exchanger was then agitated for 5 hours with 2-molar NaCl solution at 40° C. and then vacuum-filtered and washed with 2-molar NaCl solution. The solution evolving from the eluting step was combined with the washing solution and precipitated with 1.5 times the volume of methanol. The precipitate was removed by centrifuging, and then washed first with about 50 ml. of water-methanol (1+1.5 parts by volume) and then with about 50 ml. of methanol, and thereafter was dried.

Yield: 1.91 g. of Na heparinate with 202 U.S.P. units per milligram.

EXAMPLE 8

15 g. of a sodium heparinate, obtained according to Example 7 and having about 200 U.S.P. units per mg. was dissolved in 200 ml. of 2-molar NaCl solution. The solution was passed over a vacuum filter, and the residue was washed first with 30 ml. of 2-molar NaCl solution and then with about 250 ml. of fully demineralized water. The combined solutions were then brought to a chloride molarity of 0.9 with fully demineralized water. At this point in time, the purification with one liter of Lewatit CA 9249 was repeated analogously to Example 7.

The combined elution and washing solution was further processed as described above. After washing and drying of the precipitate, the yield was 11.1 g. of sodium heparinate, having an activity of 254 U.S.P. units per milligram.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of extracting heparin from a heparin-containing source which comprises extracting heparin from intestinal brine which is produced by dewatering and preservation treatment of heparin-containing animal intestines whose mucosa has been removed, said dewatering and preservation treatment consisting essentially of treating said intestines with sodium chloride.

2. The method of claim 1 wherein said dewatering and preservation treatment comprises treating non-dewatered heparin-containing animal intestines from which the mucosa has been removed, with NaCl for 2 hours to 2 days, thereby forming a heparin-containing intestinal brine having an NaCl concentration of 1–5.4 M.

3. The method of claim 2 wherein the salt treatment of the animal intestines is by addition of solid sodium chloride directly to the intestines.

4. The method of claim 2 wherein the salt treatment of the animal intestines is by immersion of the animal intestines in an aqueous solution of sodium chloride having an NaCl concentration of 1–5.4 M.

5. The method of claim 2 wherein the animal tissue has not previously been treated with sodium chloride.

6. The method of claim 1 which comprises separating the animal intestines from said intestinal brine prior to the extraction of the heparin from the brine.

7. The method of claim 6 which further comprises washing the separated animal intestines with water and adding the resultant washings to the separated intestinal brine prior to the heparin extracting step.

8. The method of claim 1 which comprises extracting heparin from said intestinal brine by acidifying the brine to a pH of 3.1–3.2.

9. The method of claim 1 wherein said intestines are those of pigs, cattle or sheep.

10. A method of extracting heparin from a heparin-containing source which consists essentially of
    treating heparin-containing animal intestines, which have been freed from mucosa but have not been subjected to NaCl treatment, with NaCl for purposes of dewatering and preservation, thereby forming an intestinal brine; and
    extracting heparin from the intestinal brine according to any of claims 1–9.

11. A method of extracting heparin from a heparin-containing source which consists essentially of separating mucosa from heparin containing animal intestines and then carrying out the method of claim 10.

* * * * *